(12) United States Patent
Alden et al.

(10) Patent No.: US 7,033,371 B2
(45) Date of Patent: Apr. 25, 2006

(54) ELECTRIC LANCET ACTUATOR

(75) Inventors: Don Alden, Sunnyvale, CA (US); Dominique M. Freeman, La Honda, CA (US)

(73) Assignee: Pelikan Technologies, Inc., Palo Alto, CA (US)

( * ) Notice: Subject to any disclaimer, the term of this patent is extended or adjusted under 35 U.S.C. 154(b) by 235 days.

(21) Appl. No.: 10/221,046

(22) PCT Filed: Jun. 12, 2002

(86) PCT No.: PCT/US02/19058

§ 371 (c)(1),
(2), (4) Date: Sep. 4, 2002

(87) PCT Pub. No.: WO02/100460

PCT Pub. Date: Dec. 19, 2002

(65) Prior Publication Data

US 2003/0233113 A1     Dec. 18, 2003

(51) Int. Cl.
*A61B 17/14* (2006.01)

(52) U.S. Cl. ...................... 606/181; 606/167
(58) Field of Classification Search ............. 606/1, 606/167, 185, 187, 169, 180, 181, 186, 108; 604/22, 44, 156, 164.01, 170.02, 264, 272, 604/19; 600/562–584
See application file for complete search history.

(56) References Cited

U.S. PATENT DOCUMENTS

| | | | |
|---|---|---|---|
| 2,714,890 A | 8/1955 | Vang | |
| 3,086,288 A | 4/1963 | Balamuth et al. | |
| 3,208,452 A | 9/1965 | Stern | |
| 3,673,475 A | 6/1972 | Britton, Jr. | |
| 3,832,776 A | 9/1974 | Sawyer | |
| 4,077,406 A | 3/1978 | Sandhage et al. | |
| 4,154,228 A | 5/1979 | Feldstein et al. | |
| 4,203,446 A | 5/1980 | Höfert et al. | |
| 4,223,674 A | 9/1980 | Fluent et al. | |
| 4,230,118 A | 10/1980 | Holman et al. | |
| 4,356,826 A | 11/1982 | Kubota | |
| 4,449,529 A | 5/1984 | Burns et al. | |
| 4,462,405 A | 7/1984 | Ehrlich | |
| 4,518,384 A | 5/1985 | Tarello et al. | |
| 4,535,773 A | 8/1985 | Yoon | |
| 4,553,541 A | 11/1985 | Burns et al. | |
| 4,627,445 A | 12/1986 | Garcia et al. | |
| 4,637,403 A | 1/1987 | Garcia et al. | |
| 4,653,513 A | 3/1987 | Dombrowski | |

(Continued)

FOREIGN PATENT DOCUMENTS

JP         2-326247         11/1990

(Continued)

OTHER PUBLICATIONS

International Search Report for PCT/US02/19053 (1pg.).
International Search Report for PCT/US02/19058 (1pg.).

*Primary Examiner*—Glenn K. Dawson
(74) *Attorney, Agent, or Firm*—Heller Ehrman LLP

(57) ABSTRACT

An electric lancet actuator and method of using same. An embodiment provides control of a lancet used for sampling blood by puncturing the skin. The lancet can be contained within a stationary housing which interacts with the proximal or driving end of lancet and allows the distal or front end of the lancet to protrude beyond the stationary housing and puncture the skin. Electric field coils or solenoids drive the lancet using either magnetic attraction or repulsion.

18 Claims, 3 Drawing Sheets

U.S. PATENT DOCUMENTS

| | | |
|---|---|---|
| 4,750,489 A | 6/1988 | Berkman et al. |
| 4,787,398 A | 11/1988 | Garcia et al. |
| 4,794,926 A | 1/1989 | Munsch et al. |
| 4,823,806 A | 4/1989 | Bajada |
| 4,895,156 A | 1/1990 | Schulze |
| 4,924,879 A | 5/1990 | O'Brien |
| 4,983,178 A | 1/1991 | Schnell |
| 4,995,402 A | 2/1991 | Smith et al. |
| 5,029,583 A | 7/1991 | Meserol et al. |
| 5,035,704 A | 7/1991 | Lambert et al. |
| 5,047,044 A | 9/1991 | Smith et al. |
| 5,097,810 A | 3/1992 | Fishman et al. |
| 5,145,565 A | 9/1992 | Kater et al. |
| 5,152,775 A | 10/1992 | Ruppert |
| 5,188,118 A | 2/1993 | Terwilliger |
| 5,189,751 A | 3/1993 | Giuliani et al. |
| 5,222,504 A | 6/1993 | Solomon |
| 5,231,993 A | 8/1993 | Haber et al. |
| 5,279,294 A | 1/1994 | Anderson et al. |
| 5,318,583 A | 6/1994 | Rabenau et al. |
| 5,320,808 A | 6/1994 | Holen et al. |
| 5,368,047 A | 11/1994 | Suzuki et al. |
| 5,395,387 A | 3/1995 | Burns |
| 5,415,169 A | 5/1995 | Siczek et al. |
| 5,472,427 A | 12/1995 | Rammler |
| 5,474,084 A | 12/1995 | Cunniff |
| 5,510,266 A | 4/1996 | Bonner et al. |
| 5,514,152 A | 5/1996 | Smith |
| 5,529,074 A | 6/1996 | Greenfield |
| 5,575,403 A | 11/1996 | Charlton et al. |
| 5,630,986 A | 5/1997 | Charlton et al. |
| 5,632,410 A | 5/1997 | Moulton et al. |
| 5,657,760 A | 8/1997 | Ying et al. |
| 5,700,695 A | 12/1997 | Yassinzadeh et al. |
| 5,714,390 A | 2/1998 | Hallowitz et al. |
| 5,720,924 A | 2/1998 | Eikmeier et al. |
| 5,738,244 A | 4/1998 | Charlton et al. |
| 5,758,643 A | 6/1998 | Wong et al. |
| 5,776,157 A | 7/1998 | Thorne et al. |
| 5,779,365 A | 7/1998 | Takaki |
| 5,788,651 A | 8/1998 | Weilandt |
| 5,800,781 A | 9/1998 | Gavin et al. |
| 5,801,057 A | 9/1998 | Smart et al. |
| 5,810,199 A | 9/1998 | Charlton et al. |
| 5,823,973 A | 10/1998 | Racchini et al. |
| 5,830,219 A | 11/1998 | Bird et al. |
| 5,846,490 A | 12/1998 | Yokota et al. |
| 5,854,074 A | 12/1998 | Charlton et al. |
| 5,855,801 A | 1/1999 | Lin et al. |
| 5,860,922 A | 1/1999 | Gordon et al. |
| 5,863,800 A | 1/1999 | Eikmeier et al. |
| 5,871,494 A | 2/1999 | Simons et al. |
| 5,879,311 A | 3/1999 | Duchon et al. |
| 5,880,829 A | 3/1999 | Kauhaniemi et al. |
| 5,885,211 A | 3/1999 | Eppstein et al. |
| 5,891,053 A | 4/1999 | Sesekura |
| 5,916,229 A | 6/1999 | Evans |
| 5,935,075 A | 8/1999 | Casscells et al. |
| 5,938,679 A | 8/1999 | Freeman et al. |
| 5,951,582 A | 9/1999 | Thorne et al. |
| 5,968,063 A | 10/1999 | Chu et al. |
| 5,971,941 A | 10/1999 | Simons et al. |
| 5,997,561 A | 12/1999 | Böcker et al. |
| 6,027,459 A | 2/2000 | Shain et al. |
| 6,036,924 A | 3/2000 | Simons et al. |
| 6,048,352 A | 4/2000 | Douglas et al. |
| 6,071,294 A | 6/2000 | Simons et al. |
| 6,093,156 A | 7/2000 | Cunningham et al. |
| 6,117,630 A | 9/2000 | Reber et al. |
| 6,120,462 A | 9/2000 | Hibner et al. |
| 6,132,449 A | 10/2000 | Lum et al. |
| 6,136,013 A | 10/2000 | Marshall et al. |
| 6,139,562 A * | 10/2000 | Mauze et al. ............... 606/171 |
| 6,143,164 A | 11/2000 | Heller et al. |
| 6,152,875 A | 11/2000 | Hakamata |
| 6,152,942 A | 11/2000 | Brenneman et al. |
| 6,155,992 A | 12/2000 | Henning et al. |
| 6,156,051 A | 12/2000 | Schraga |
| 6,159,424 A | 12/2000 | Kauhaniemi et al. |
| 6,171,325 B1 | 1/2001 | Mauze et al. |
| 6,176,865 B1 | 1/2001 | Mauze et al. |
| 6,183,489 B1 | 2/2001 | Douglas et al. |
| 6,193,673 B1 | 2/2001 | Viola et al. |
| 6,203,504 B1 | 3/2001 | Latterell et al. |
| 6,206,841 B1 | 3/2001 | Cunningham et al. |
| 6,210,420 B1 | 4/2001 | Mauze et al. |
| 6,210,421 B1 | 4/2001 | Böcker et al. |
| 6,228,100 B1 | 5/2001 | Schraga |
| 6,231,531 B1 | 5/2001 | Lum et al. |
| 6,261,241 B1 | 7/2001 | Burbank et al. |
| 6,261,245 B1 | 7/2001 | Kawai et al. |
| 6,283,926 B1 | 9/2001 | Cunningham et al. |
| 6,285,454 B1 | 9/2001 | Douglas et al. |
| 6,306,104 B1 | 10/2001 | Cunningham et al. |
| 6,306,152 B1 * | 10/2001 | Verdonk et al. ............ 606/182 |
| 6,315,738 B1 | 11/2001 | Nishikawa et al. |
| 6,319,210 B1 | 11/2001 | Douglas et al. |
| 6,332,871 B1 | 12/2001 | Douglas et al. |
| 6,352,514 B1 | 3/2002 | Douglas et al. |
| 6,364,889 B1 | 4/2002 | Kheiri et al. |
| 6,364,890 B1 | 4/2002 | Lum et al. |
| 6,375,627 B1 | 4/2002 | Mauze et al. |
| 6,379,317 B1 | 4/2002 | Kintzig et al. |
| 6,379,969 B1 | 4/2002 | Mauze et al. |
| 6,391,005 B1 | 5/2002 | Lum et al. |
| 6,402,701 B1 | 6/2002 | Kaplan et al. |
| 6,402,704 B1 | 6/2002 | McMorrow |
| 6,409,740 B1 | 6/2002 | Kuhr et al. |
| 6,461,496 B1 | 10/2002 | Feldman et al. |
| 6,472,220 B1 | 10/2002 | Simons et al. |
| 6,485,439 B1 | 11/2002 | Roe et al. |
| 6,488,891 B1 | 12/2002 | Mason et al. |
| 6,491,709 B1 | 12/2002 | Sharma et al. |
| 6,497,845 B1 | 12/2002 | Sacherer |
| 6,503,210 B1 | 1/2003 | Hirao et al. |
| 6,506,575 B1 | 1/2003 | Knappe et al. |
| 6,530,892 B1 | 3/2003 | Kelly |
| 2001/0031931 A1 | 10/2001 | Cunningham et al. |
| 2002/0002344 A1 | 1/2002 | Douglas et al. |
| 2002/0004196 A1 | 1/2002 | Whitson |
| 2002/0052618 A1 | 5/2002 | Haar et al. |
| 2002/0082543 A1 | 6/2002 | Park et al. |
| 2002/0103499 A1 | 8/2002 | Perez et al. |
| 2003/0073071 A1 * | 4/2003 | Boecker et al. ............. 600/573 |
| 2003/0083685 A1 * | 5/2003 | Freeman et al. ............ 606/181 |
| 2003/0088191 A1 * | 5/2003 | Freeman et al. ............ 600/583 |
| 2003/0191415 A1 * | 10/2003 | Moerman et al. ........... 600/584 |

FOREIGN PATENT DOCUMENTS

| | | |
|---|---|---|
| JP | HEI 4 - 194660 | 7/1992 |
| JP | 9-276235 | 10/1997 |
| JP | 10-296325 | 10/1998 |
| JP | 2000-11768 | 4/2000 |
| WO | WO 93/02720 | 2/1993 |
| WO | WO 93/12726 | 7/1993 |
| WO | WO 97/42888 | 11/1997 |
| WO | WO 01/00090 A1 | 1/2001 |
| WO | WO 01/34029 | 5/2001 |
| WO | WO 01/66010 A1 | 9/2001 |
| WO | WO 02/056769 A1 | 7/2002 |

* cited by examiner

ELECTRIC LANCET ACTUATOR

RELATED APPLICATIONS

This application is a National Stage filed under 35 USC § 371 of PCT Application No. PCT/US02/19058 filed Jun. 12, 2002, which claims priority under 35 USC § 119, to U.S. Provisional Application No. 60/298,055 filed Jun. 12, 2001, the entire disclosures of which are hereby expressly incorporated by reference.

TECHNICAL FIELD

Lancing devices are known in the medical health-care products industry for piercing the skin to produce blood for analysis. Biochemical analysis of blood samples is a diagnostic tool for determining clinical information. Many point-of-care tests are performed using capillary whole blood, the most common being monitoring diabetic blood glucose level. Other uses for this method include the analysis of oxygen and coagulation based on Prothrombin time measurement. Typically, a drop of blood for this type of analysis is obtained by making a small incision in the fingertip, creating a small wound, which generates a small blood droplet on the surface of the skin.

BACKGROUND ART

Early methods of lancing included piercing or slicing the skin with a needle or razor. Current methods utilize lancing devices that contain a multitude of spring, cam and mass actuators to drive the lancet. These include cantilever springs, diaphragms, coil springs, as well as gravity plumbs used to drive the lancet. Typically, the device is pre-cocked or the user cocks the device. The device is held against the skin and mechanically triggers the ballistic launch of the lancet. The forward movement and depth of skin penetration of the lancet is determined by a mechanical stop and/or dampening, as well as a spring or cam to retract the lancet. What has been needed is a lancet and method of using the lancet that provides a desired amount of control over the lancing procedure.

DISCLOSURE OF INVENTION

Embodiments of the present invention are related to medical health-care products and to methods for obtaining body fluids for chemical analysis. More particularly, embodiments of the invention relate to devices and methods for piercing the skin (lancing) using an electrically driven lancet.

In an embodiment of the invention, an electric lancet actuator provides drive control of the lancet used for sampling blood by puncturing the skin. The lancet is contained within a stationary housing, which interacts with the proximal or driving end of the lancet, and allows the distal or front end of the lancet to protrude beyond the stationary housing and puncture the skin. Electric field coils drive the lancet using either magnetic attraction or repulsion. An iron flag or iron core or other magnetically permeable material is attached to the lancet to complete the magnetic circuit of the field coils. The iron flag is perforated with slits to create the magnetic bars of the same pitch as the field coils. An insulating housing provides a smooth low friction guide surface for the flag, and protects the lancet from touching the electric field coils and conducting electric current to the skin. Rivets, which connect the insulating housing to the stationary housing, bridge between the electric field coils and behave as poles.

A method for sampling blood through the skin uses the electric lancet driver to puncture the skin and retract the lancet with control on both the entry and the exit of the lancet from the skin.

BRIEF DESCRIPTION OF DRAWING

The objects, advantages and features of this invention will be more readily appreciated from the following detailed description, when read in conjunction with the accompanying drawing, in which.

BEST MODE FOR CARRYING OUT THE INVENTION

Variations in skin thickness (stratum corneum) and hydration of the epidermis can yield different results from different users of existing lancing devices. Current devices rely on adjustable mechanical stops or damping, to control the lancet's depth of penetration.

Figure 1A:
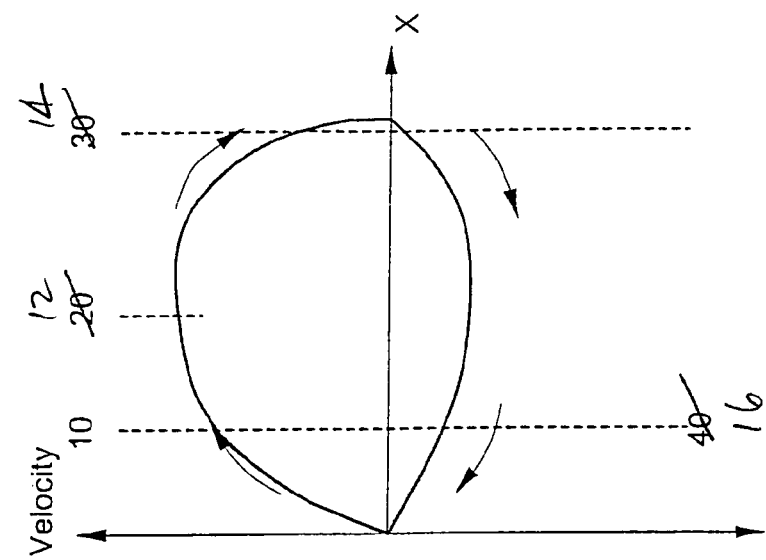
FIGS. 1A–1C are graphs of lancet velocity versus position for spring driven, cam driven, and electrically driven actuation methods.
Figure 1B:
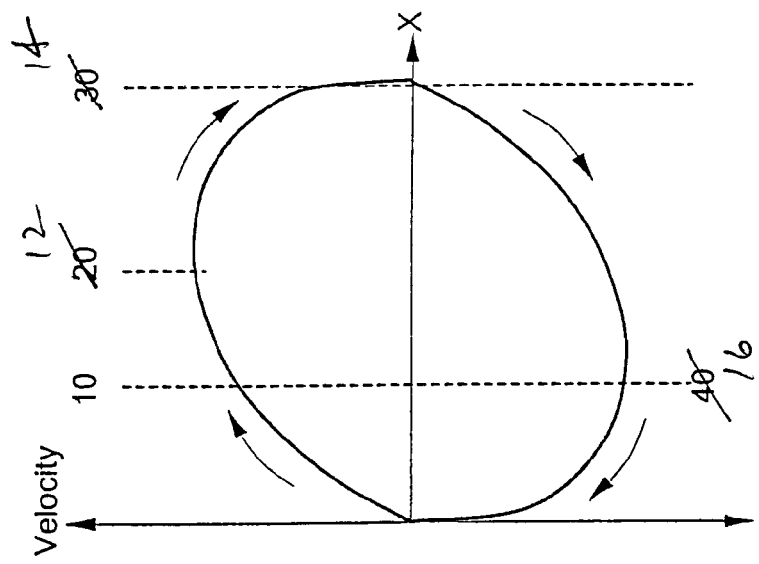

Common displacement profiles for both spring driven and cam driven devices are shown in FIGS. 1A and 1B, respectively. Velocity is plotted against displacement (X) of the lancet. FIG. 1A represents typical spring driven devices (e.g. Becton Dickinson launcher). The lancet exit velocity increases until the lancet hits the surface of the skin (10). Because of the tensile characteristics of the skin, it will bend or deform until the lancet tip cuts the surface (12), the lancet will then penetrate the skin until it reaches a full stop (14). At this point displacement is maximal (limit of penetration) and the lancet stops. Mechanical stops absorb excess energy from the actuator and transfer it to the lancet body. The energy can cause both recoil resulting in multiple piercing (as seen by coiled profile in FIG. 1A) and unnecessary pain as well as transferring vibratory energy into the skin and exciting nerve endings causing unnecessary pain. Retraction of the lancet then occurs and the lancet exits the skin (16) to return into the housing. Because of this type of spring driven actuation mechanism, velocity cannot be controlled.

FIG. 1B shows that cam driven devices (such as Softclix®) have similar velocity versus displacement profiles, but because the return path is specified in the cam configuration, there is no possibility of multiple firings from one actuation. Cam based devices do offer some level of control of lancet velocity, but are unable to compensate for individual skin characteristics.

Figure 1C:
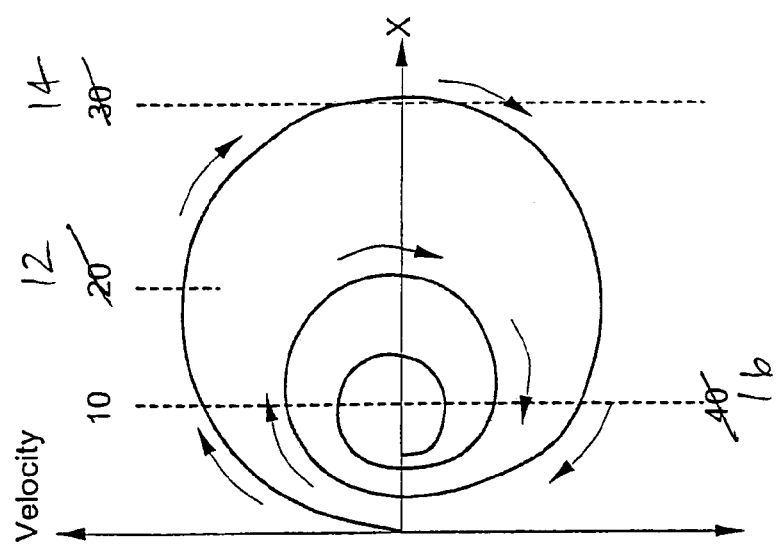

Advantages are achieved by utilizing an electric drive as an actuator for the lancet to achieve a velocity versus position profile as shown in FIG. 1C. Embodiments of the present invention allow for the ability to accurately control depth of penetration, to control lancet withdrawal velocity, and reduce the pain perceived when cutting into the skin. Embodiments of the invention can be used with position feedback to control the power delivered to the lancet and optimize the velocity and displacement profile to compensate for variations in skin thickness and hydration, as described in a copending U.S. Pat. application Ser. No. 60/298,001, filed Jun. 12, 2001 Inventors: Dominique Freeman, et al., entitled "SELF OPTIMIZING LANCING DEVICE WITH ADAPTATION MEANS TO TEMPORAL VARIATIONS IN CUTANEOUS PROPERTIES") submitted on the same day and assigned to the same assignee as the present application. Said copending application is incorporated by reference in its entirety herein.

Pain reduction is achieved through both the rapid lancet cutting speed and a lightweight lancet. The rapid cutting minimizes the shock waves produced when the lancet strikes the skin in addition to compressing the skin for efficient cutting. Due to the very light mass of the lancet and lack of a mechanical stop, there is no vibrational energy transferred to the finger during cutting.

The lancing devices such as those whose velocity versus position profiles one shown in FIGS. 1A and 1B typically yield 70–80% success rate in obtaining a blood droplet, as some lancing events are unsuccessful. Success rate is dependent on reaching the blood capillaries and venuoles which yield the blood sample. Due to variations in skin thickness and hydration, some types of skin will deform more before cutting starts, and hence the actual depth of penetration will be less, resulting in less capillaries and venuoles cut. An electric lancet actuator controls the depth of penetration and hence improves the success rate of blood yield. Furthermore, the electric lancet allows slower retraction of the lancet, as described in a copending appijoatien U.S. patent application Ser. No. 60/297,861, filed Jun. 12, 2001 (Attorney Docket Number 38187-2556, Inventors: Blocker, et al., entitled "METHOD AND APPARATUS FOR IMPROVING SUCCESS RATE OF BLOOD YIELD FROM A FINGERTIP") submitted on the same day and assigned to the same assignee as the present application. Said copending application is incorporated by reference in its entirety herein.

Spontaneous blood yield occurs when blood from the cut vessels flow up the wound tract to the surface of the skin, where it can be collected and tested. Tissue elasticity parameters may force the wound tract to close behind the retracting lancet preventing the blood from reaching the surface. If however, the lancet were to be withdrawn slowly from the wound tract, thus keeping the wound open, blood could flow up the patent channel. Hence the ability to control the lancet speed into and out of the wound allows the device to compensate for changes in skin thickness and variations in skin hydration and thereby achieves spontaneous blood yield with maximum success rate while minimizing pain.

Electronic actuation is achieved by using an electromagnetic driver coupled directly to the lancet minimizing the mass of the lancet and allowing the driver to bring the lancet to a stop at a predetermined depth without the use of a mechanical stop. Alternatively, if a mechanical stop is required for positive positioning, the energy transferred to the stop can be minimized. The electromagnetic driver allows programmable control over the entire lancing process including timing the start of the lancet, tracking the lancet position, measuring the lancet velocity, controlling the distal stop acceleration, and controlling the skin penetration depth.

Figure 2:
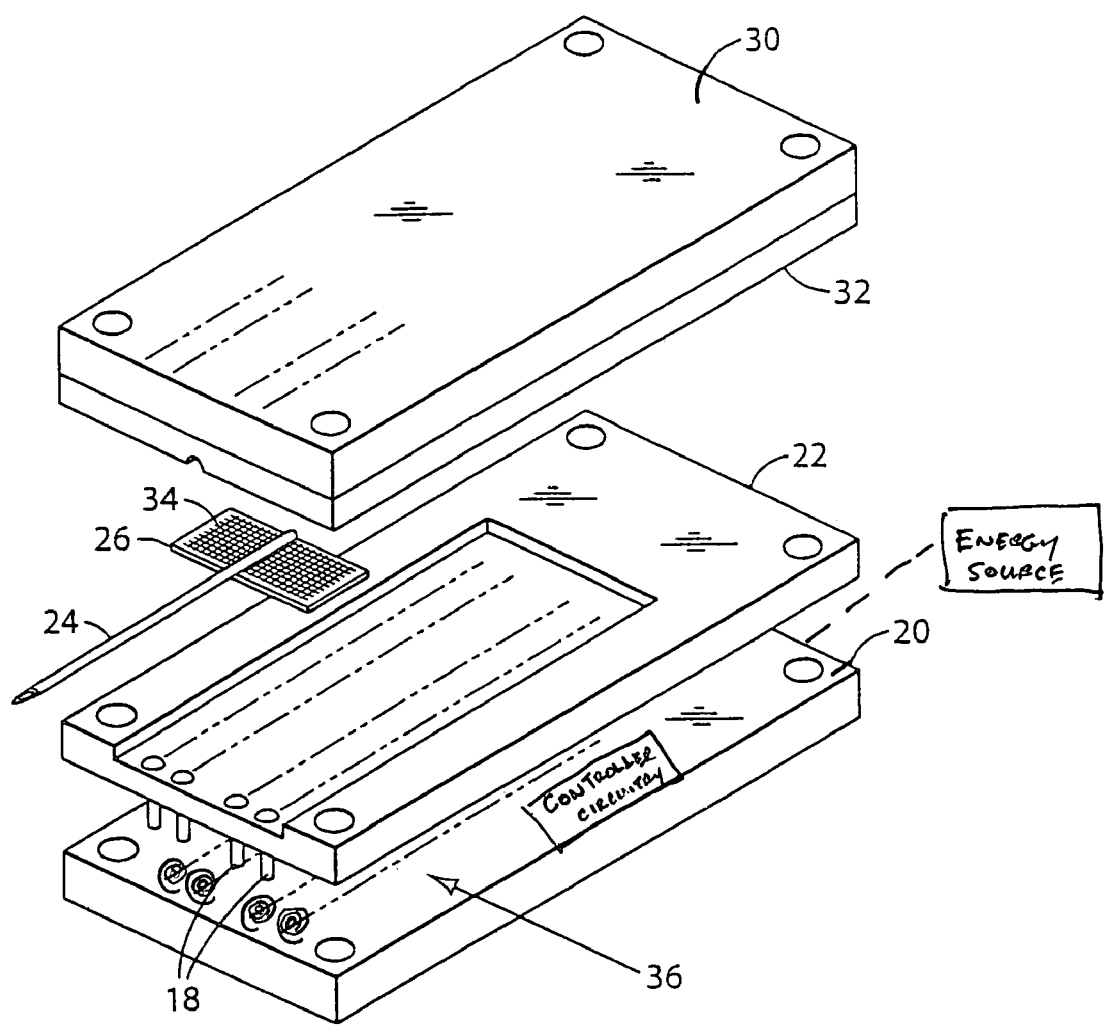
FIG. 2 illustrates a flat electric lancet actuator using a solenoid configuration to drive the lancet.
Figure 3:
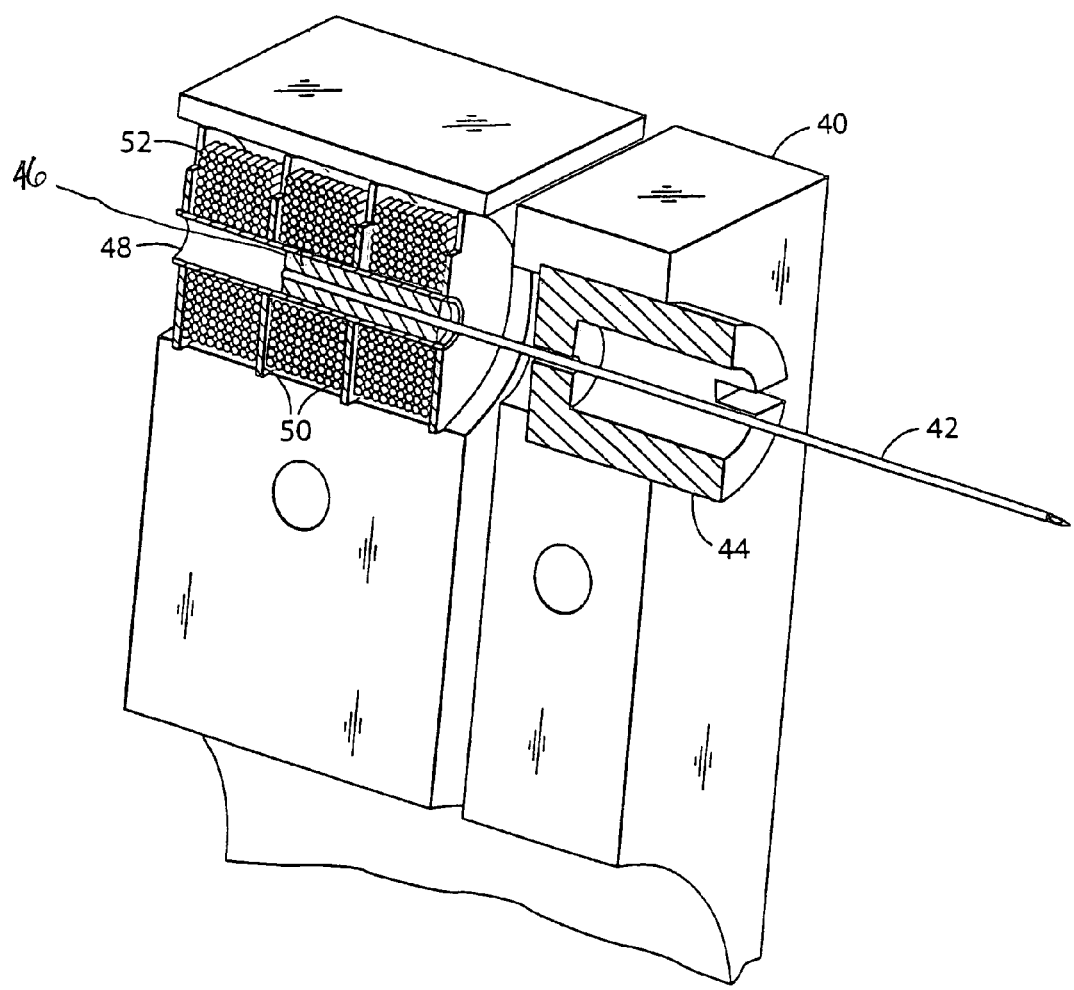
FIG. 3 illustrates a cylindrical electric lancet actuator using a different configuration of solenoid to drive tile lancet.

Reference will now be made in detail to the exemplary embodiments of the invention, examples of which are illustrated in FIGS. 2 and 3. Wherever possible, the same reference numbers will be used throughout the drawings to refer to the same or like parts.

FIG. 2 depicts an embodiment for the electric lancet actuator. Lancet is defined generally to include any sharp or blunt member, preferably having a relatively low mass, used to puncture the skin for the purpose of cutting blood vessels and allowing blood to flow to the surface of the skin. Electric lancet actuator is defined generally to include any device that moves a lancet under an electrically induced force. FIG. 2 is a partially exploded view of an electric lancet actuator. The top half of the driver is shown assembled. The bottom half of the driver is shown exploded for illustrative purposes.

FIG. 2 shows the inner insulating housing (22) separated from the stationary housing (20), and the lancet (24) and flag (26) assembly separated from the inner insulating housing (22) for illustrative purposes. In addition, only four rivets (18) are shown as attached to the inner insulating housing (22) and separated from the stationary housing (20). In an embodiment, each coil drive field core in the PC board located in the stationary housing (20) and (30) is connected to the inner insulating housing (22) and (32) with rivets.

The electric lancet actuator has a moving part comprising a lancet assembly with a lancet (24) and a magnetically permeable flag (26) attached at the proximal or drive end and a stationary part comprising a stationary housing assembly with electric field coils arranged so that they produce a balanced field at the flag to reduce or eliminate any net lateral force on the flag. Electric field coil means one or more metal coils which generate a magnetic field when electric current passes through the metal. Iron flag is generally defined to mean any flat or enlarged piece of magnetic material which increases the surface area of the lancet assembly to enhance the electromotive forces generated between the proximal end of the lancet and the field coils. Preferably, the combined mass of the lancet and the iron flag are minimized to facilitate rapid acceleration for introduction into the skin, to reduce the impact when the lancet stops in the skin, and to facilitate prompt velocity profile changes throughout the sampling cycle.

The stationary housing assembly consists of a lower stationary housing (20), a lower inner insulating housing (22), an upper inner insulating housing (32), an upper stationary housing (30), and rivets (18) assembled into a single unit. The lower and upper inner insulating housing (22) and (32) are relieved to form a slot so that lancet assembly can be slid into the driver assembly from the side perpendicular to the direction of the lancet's advancement and retraction. This allows the disposal of the lancet assembly and reuse of the stationary housing assembly with another lancet assembly while avoiding accidental lancet launches during replacement.

The electric field coils in the upper and lower stationary housing (20) and (30) are fabricated in a multi-layer printed circuit (PC) board. They may also be conventionally wound wire coils. A Teflon® (or other lubricious insulating material) is used to construct the lower and upper inner insulating housing (22) and (32). Each insulating housing is mounted on the PC board to provide electrical insulation and physical protection, as well as to provide a low-friction guide for the lancet. The lower and upper inner insulating housing (22) and (32) provide a reference surface with a small gap so that the lancet assembly (24) and (26) can align with the drive field coils in the PC board for good magnetic coupling. Rivets (18) connect the lower inner insulating housing (22) to the lower stationary housing (20) and are made of magnetically permeable material such as ferrite or steel, which serves to concentrate the magnetic field. This mirrors the construction of the upper inner insulating housing (32) and upper stationary housing (30). These rivets form the poles of the electric field coils. The PC board is fabricated with multiple layers of coils or with multiple boards. Each layer supports spiral traces around a central hole. Alternate layers spiral from the center outwards or from the edges inward. In this way each layer connects via simple feedthrough holes, and the current always travels in the same direction, summing the ampere-turns.

The PC boards within the lower and upper stationary housings (20) and (30) are connected to the lower and upper inner insulating housings (22) and (32) with the rivets (18). The lower and upper inner insulating housings (22) and (32) expose the rivet heads on opposite ends of the slot where the lancet assembly (24) and (26) travels. The magnetic field lines from each rivet create magnetic poles at the rivet heads. An iron bar on the opposite side of the PC board within each of the lower and upper stationary housing (20) and (30) completes the magnetic circuit by connecting the rivets. To complete the magnetic circuit an iron bar is needed between the rivets of a magnetic coil pair. In operation, the magnetically permeable flag (26) attached to the lancet (24) is divided into slits and bars (34). The slit patterns are staggered so that the flag (26) can be driven by coils in two, three or more phases.

Both lower and upper stationary housing (20) and (30) contain PC boards so that there is a symmetrical magnetic field above and below the flag (26). When the pair of PC boards is turned on, a magnetic field is established around the bars between the slits of the magnetically permeable iron on the flag (26). The bars experiences a force that tends to move the magnetically permeable material to a position minimizing the number and length of magnetic field lines and conducting the magnetic field lines between the magnetic poles.

When a bar of the flag (26) is centered between the rivets (18) of a magnetic pole, there is no net force on the flag, and any disturbing force is resisted by imbalance in the field. This embodiment of the device operates on a principle similar to that of a solenoid. Solenoids cannot push by repelling iron; they can only pull by attracting the iron into a minimum energy position. The slits (34) on one side of the flag (26) are offset with respect to the other side by approximately one half of the pitch of the poles. By alternately activating the coils on each side of the PC board, the lancet assembly can be moved with respect to the stationary housing assembly. The direction of travel is established by selectively energizing the coils adjacent the metal flag on the lancet assembly. Alternatively, a three phase, three-pole design or a shading coil that is offset by one-quarter pitch establishes the direction of travel. The lower and upper stationary housing (20) and (30) shown in FIG. 2 contain the PC boards with electric field coils, which drive the lancet assembly and the circuitry for controlling the entire electric lancet activator.

The embodiment described above is a magnetic attraction drive, similar to commonly available circular stepper motors (Hurst Manufacturing BA Series motor, or "Electrical Engineering Handbook" Second edition p 1472–1474, 1997). These references are hereby incorporated by reference. Another embodiment is a linear induction drive that uses a changing magnetic field to induce electric currents in the lancet assembly. These induced currents produce a secondary magnetic field that repels the primary field and applies a net force on the lancet assembly. The linear induction drive uses an electrical drive control that sweeps a magnetic field from pole to pole, propelling the lancet before it. Varying the rate of the sweep and the magnitude of the field by altering the driving voltage and frequency controls the force applied to the lancet assembly and its velocity. The arrangement of the coils and rivets to concentrate the magnetic flux also apply to the induction design creating a growing magnetic field as the electric current in the field switches on. This growing magnetic field creates an opposing electric current in the conductive flag. In a linear induction motor the flag is electrically conductive, and its magnetic properties are unimportant. Copper or aluminum are materials that can be used for the conductive flags. Copper is generally used because of its good electrical conductivity. The opposing electrical field produces an opposing magnetic field that repels the field of the coils. By phasing the power of the coils, a moving field can be generated which pushes the flag along just below the synchronous speed of the coils. By controlling the rate of sweep, and by generating multiple sweeps, the flag can be moved at a desired speed.

FIG. 3 shows another solenoid type electric lancet actuator that is capable of driving an iron core mounted to the lancet assembly using a direct current (DC) power supply. The solenoid is divided into three separate coils along the path of the lancet, two end coils and a middle coil. Direct current is alternated to the coils to advance and retract the lancet.

The stationary iron housing (40) contains the solenoid whose first coil (52) is flanked by iron spacers (50) which concentrate the magnetic flux at the inner diameter creating magnetic poles. The inner insulating housing (48) isolates the lancet (42) and iron core (46) from the solenoids (52) and provides a smooth, low friction guide surface. The lancet (42) and iron core (46) are further centered by the lancet guide (44). The lancet (42) is protracted and retracted by alternating the current between the first coil (52), the middle coil, and the third coil to attract or repulse the iron core (46). The lancet is retracted by reversing the coil sequence and attracting the core and lancet back into the housing. The lancet guide (44) also serves as a stop for the iron core (46) mounted to the lancet (42).

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. An electric lancet actuator comprising:
   a lancet with a distal puncture end and proximal driver end housed within a stationary housing, said housing comprising an electric energy source for driving said lancet along a predetermined path;
   a plurality of electric field coils,
   a metal core; and
   a controller for selectively providing current from the electric energy source to the plurality of coils in sequence to move the metal core which in turn moves the lancet along the predetermined path.

2. An electric lancet actuator according to claim 1 wherein:
   said stationary housing further comprises iron spacers coupled to the electric field coils.

3. An electric lancet actuator according to claim 1 wherein:
   an inner insulating housing separates said electric field coils from said lancet.

4. An electric lancet actuator according to claim 3 wherein:
   said inner insulating housing contains rivets such that magnetic poles extend toward said lancet.

5. An electric lancet actuator according to claim 1 or claim 4 wherein:
   a metal flag is attached at the proximal driver end of said lancet.

6. An electric lancet actuator according to claim 5 wherein:
said metal flag is perforated with slits.

7. An electric lancet actuator according to claim 1 wherein:
said electric field coils are disposed on a printed circuit board.

8. An electric lancet actuator according to claim 1 wherein:
said electric field coils move said lancet by generating an electromotive force.

9. An electric lancet actuator according to claim 1 wherein:
said electric field coils drive said lancet by application of alternating electromagnetic polarities.

10. An electric lancet actuator according to claim 1 wherein:
said electric field coils are configured as concentric solenoid coils.

11. An electric lancet actuator according to claim 10 wherein:
an inner insulating housing separates said solenoid coils and said lancet.

12. An electric lancet actuator according to claim 10 or claim 11 wherein:
said metal core is attached at the proximal driver end of said lancet.

13. An electric lancet actuator according to claim 10 wherein:
said solenoid coils move said movable lancet by generating an electromotive force.

14. An electric lancet actuator according to claim 10 wherein:
said solenoid coils drive said movable lancet by application of alternating electromagnetic polarities.

15. An electric lancet actuator according to claim 1 wherein:
said lancet is removable from said stationary housing and is disposable.

16. The device of claim 1 wherein the controller advances the lancet along a path into the tissue and then removes the lancet from the tissue.

17. An electric lancet actuator comprising:
a lancet for puncturing a piece of skin to cause the formation of a droplet of blood;
a source for generating electromagnetic energy to displace said lancet;
and circuitry for alternating current between a first coil, a middle coil, and a third coil in the source to move said lancet.

18. A method for sampling blood through a piece of skin comprising the steps of:
advancing a lancet with electromagnetic force from an electric lancet actuator to propel a lancet into said skin by activating subsets of a plurality of coils in the actuator in sequence to advance the lancet; and
retracting said lancet with electromagnetic force from said electric lancet actuator by reversing the sequence of coil activation.

* * * * *